(12) United States Patent
Lange et al.

(10) Patent No.: US 9,217,115 B2
(45) Date of Patent: Dec. 22, 2015

(54) USE OF TETRAHYDROBERIZOXAZINES AS STABILISERS

(75) Inventors: Arno Lange, Bad Duerkheim (DE); Helmut Mach, Heidelberg (DE); Hans Peter Rath, Gruenstadt (DE); Dietmar Posselt, Heidelberg (DE)

(73) Assignee: BASF SE, Ludwigshafen (DE)

( * ) Notice: Subject to any disclaimer, the term of this patent is extended or adjusted under 35 U.S.C. 154(b) by 1054 days.

(21) Appl. No.: 11/996,078

(22) PCT Filed: Jul. 18, 2006

(86) PCT No.: PCT/EP2006/064352
§ 371 (c)(1),
(2), (4) Date: Jan. 18, 2008

(87) PCT Pub. No.: WO2007/012580
PCT Pub. Date: Feb. 1, 2007

(65) Prior Publication Data
US 2008/0196300 A1 Aug. 21, 2008

(30) Foreign Application Priority Data
Jul. 26, 2005 (DE) .......................... 10 2005 035 527

(51) Int. Cl.
| C10L 1/22 | (2006.01) |
|---|---|
| C07D 265/16 | (2006.01) |
| C10L 1/14 | (2006.01) |
| C10L 1/233 | (2006.01) |
| C10L 1/238 | (2006.01) |
| C10L 10/00 | (2006.01) |
| C10L 1/18 | (2006.01) |
| C10L 1/26 | (2006.01) |
| C10L 1/183 | (2006.01) |
| C10L 1/228 | (2006.01) |
| C10L 1/19 | (2006.01) |
| C10L 1/236 | (2006.01) |

(52) U.S. Cl.
CPC .............. *C10L 1/22* (2013.01); *C07D 265/16* (2013.01); *C10L 1/143* (2013.01); *C10L 1/18* (2013.01); *C10L 1/233* (2013.01); *C10L 1/238* (2013.01); *C10L 1/26* (2013.01); *C10L 10/00* (2013.01); *C10L 1/1832* (2013.01); *C10L 1/19* (2013.01); *C10L 1/221* (2013.01); *C10L 1/2283* (2013.01); *C10L 1/236* (2013.01); *C10L 1/2691* (2013.01); *C10L 2200/0254* (2013.01); *C10L 2200/0259* (2013.01); *C10L 2200/0268* (2013.01); *C10L 2230/081* (2013.01); *C10L 2250/04* (2013.01); *C10L 2270/04* (2013.01)

(58) Field of Classification Search
CPC ......... C10L 1/143; C10L 1/233; C10L 1/238; C10L 1/2283; C10L 10/00; C07D 265/16
USPC ............ 44/334, 329, 330, 422, 424; 508/246, 508/244, 245; 252/397, 401, 403, 405
See application file for complete search history.

(56) References Cited

U.S. PATENT DOCUMENTS

| 2,458,526 | A |   | 1/1949 | Oberright |
|---|---|---|---|---|
| 3,825,538 | A | * | 7/1974 | Reynolds ........................ 544/90 |
| 4,025,316 | A | * | 5/1977 | Stover ............................ 44/330 |
| 4,207,104 | A |   | 6/1980 | Chapman et al. |
| 4,585,728 | A |   | 4/1986 | Furutachi et al. |
| 5,876,468 | A |   | 3/1999 | Moreton |

(Continued)

FOREIGN PATENT DOCUMENTS

| DE | 19948111 A1 * | 4/2001 |
|---|---|---|
| EP | 0 376 563 A1 | 7/1990 |

(Continued)

OTHER PUBLICATIONS

D. L. Fields et al. : "Mannich-Type Condensation of Hydroquinone, Formaldehyde, and Primary Amines", Journal of Organic Chemistry, vol. 27, XP 002228613, pp. 2749-2753, 1962.

(Continued)

*Primary Examiner* — James Goloboy
*Assistant Examiner* — Latosha Hines
(74) *Attorney, Agent, or Firm* — Oblon, McClelland, Maier & Neustadt, L.L.P.

(57) ABSTRACT

The use of tetrahydrobenzoxazines I

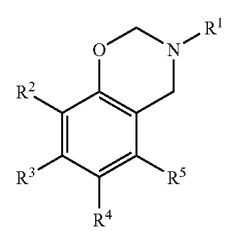

(I)

where $R^1$ is a hydrocarbyl radical and $R^2$, $R^3$, $R^4$ and $R^5$ are each independently hydrogen atoms, hydroxyl groups or hydrocarbyl radicals, and where $R^2$ to $R^5$ may also form a second and a third tetrahydrooxazine ring, with the proviso that at least one of the substituents has from 4 to 3000 carbon atoms and the remaining substituents, when they are hydrocarbyl radicals, each have from 1 to 20 carbon atoms, as stabilizers for stabilizing inanimate organic material, especially turbine fuels, against the action of light, oxygen and heat.

10 Claims, No Drawings

(56) References Cited

U.S. PATENT DOCUMENTS

| | | | |
|---|---|---|---|
| 8,016,898 B1 * | 9/2011 | Lange et al. | 44/415 |
| 2006/0025509 A1 * | 2/2006 | Zhang et al. | 524/284 |
| 2006/0196107 A1 | 9/2006 | Malfer et al. | |
| 2008/0274924 A1 * | 11/2008 | Lange et al. | 508/542 |
| 2011/0251114 A1 * | 10/2011 | Lange et al. | 508/542 |

FOREIGN PATENT DOCUMENTS

| | | |
|---|---|---|
| EP | 0 647 700 | 4/1995 |
| EP | 0 811 672 | 12/1997 |
| EP | 1 621 566 | 2/2006 |
| FR | 2 091 605 | 1/1972 |
| GB | 2 308 849 | 7/1997 |
| JP | 63 149646 | 6/1988 |
| JP | 2003 255487 | 9/2003 |
| WO | 89 05803 | 6/1989 |
| WO | WO 00/78898 A1 | 12/2000 |
| WO | 01 25293 | 4/2001 |
| WO | WO 01/25294 A1 | 4/2001 |
| WO | WO 0125294 A1 * | 4/2001 |
| WO | 01 34581 | 5/2001 |
| WO | 03 106595 | 12/2003 |
| WO | 2005 073152 | 8/2005 |
| WO | WO 2007/012580 A1 | 2/2007 |

OTHER PUBLICATIONS

K. Ho-Dong et al.: "Model Compounds Study on the Network Structure of Polybenzoxazines", Macromolecules, vol. 36, XP 002404381, pp. 8320-8329, 2003.

W. J. Burke et al. : "Mono-1,3-Benzoxazines From Hydroquinone", Journal of Organic Chemistry., vol. 28, XP 002404382, pp. 1098-1100,1963.

D. L. Reynolds et al.: "1,3,5-Trisubstituted Hexahydrotriazines as Mannich Reagents." Journal of Heterocyclic Chemistry, vol. 8, XP 002404383, pp. 611-615, 1971.

P. D. Woodgate et al.: "Synthesis of Dioxazaborocines From N-Substituted-Bis(2-Hydroxyaryl) Aminomethylamines", Journal of Organometallic Chemistry, vol. 592, XP 002404384, pp. 180-193, 1999.

U.S. Appl. No. 12/527,971, filed Aug. 20, 2009, Posselt, et al.

U.S. Appl. No. 12/669,576, filed Jan. 19, 2010, Lange, et al.

European Notice of Opposition issued Jun. 8, 2011, in Patent No. 1 910 319 (Appln. No. 06777819.1).

Request for Continued Examination filed in U.S. Appl. No. 11/996,078, on Jun. 6, 2011.

L. Q. Maurice, et al., "Advanced aviation fuels: a look ahead via a historical perspective", FUEL, vol. 80, Feb. 5, 2001, pp. 747-756.

Declaration of Bill Colucci issued Mar. 7, 2012, in European Patent No. 1 910 319 (Appln. No. 06777819.1).

Grounds of Opposition issued Jul. 2012, to European Patent No: 2239258 (Application No. 10167054.5), (with English-language Translation).

Spencer E Taylor, "Design and Current Status of Development of a Jet Fuel Thermal Stability Additive" American Institute of Aeronautics and Astronautics, 1999.

Kirklin et al, "Aviation Fuel Thermal Stability Requirements" ASTM publication code No. (PCN) 04-011380-12, 1992.

Declaration of William J. Colucci issued Nov. 22, 2013, in European Patent No. 1 910 319 (Appln. No. 06777819.1).

Harold O. Strange, Development of a Laboratory Test for Multiport Fuel Injector Deposits— Evaluation of the Jet Fuel Thermal Oxidation Test Apparatus (JFTOT), Prepared for the Coordinating Research Council, Inc., Pittsburgh Applied Research Corporation. (Dec. 1987).

Opposition Decision dated Jul. 25, 2014 issued in European Patent Application No. 06 777 819.1.

Opposition Decision dated Jul. 24, 2014 issued in European Patent Application No. 10 167 054.5.

* cited by examiner

USE OF TETRAHYDROBERIZOXAZINES AS STABILISERS

The present invention relates to the use of specific tetrahydrobenzoxazines as stabilizers for stabilizing inanimate organic material against the action of light, oxygen and heat, especially in turbine fuels jet fuels). The present invention further relates to a turbine fuel composition and to an additive concentrate for turbine fuels which comprise these tetrahydrobenzoxazines. The present invention further relates to a process for preparing these tetrahydrobenzoxazines. Since some of these tetrahydrobenzoxazines are novel substances, the present invention also relates to these novel substances themselves.

The mechanical, chemical and/or esthetic properties of inanimate organic material, for example of plastics and coatings, but also of mineral oil products and fuels, are known to be impaired by the action of light, oxygen and heat. This impairment is exhibited typically in the form of yellowing, discoloration, crack formation or embrittlement of the material. Stabilizers or stabilizer compositions with which improved protection against such impairment of organic material by light, oxygen and heat can be achieved are already known.

For instance, WO 05/073152 (1) describes 2-alkylpolyisobutenylphenols and their Mannich adducts as antioxidants for stabilizing inanimate organic material against the action of light, oxygen and heat. Other materials to be stabilized include fuels such as gasoline fuels, diesel fuels and turbine fuels, and also lubricant compositions. In turbine fuels, these 2-alkylpolyisobutenylphenols and their Mannich adducts bring about an improvement in the thermal stability and a reduction in the deposits in the fuel circuit and combustion system of the turbines.

WO 03/106595 (2) also discloses, as well as hydrocarbyl-substituted succinic acid derivatives and polyalkenylthiophosphonate esters, Mannich adducts made from hydrocarbyl-substituted phenols, an aldehyde and an amine as additives for turbine fuels (jet fuels) for improving the thermal stability and for reducing deposits.

However, especially for the mineral oil product and fuel sector, there is a need for stabilizers and antioxidants with improved protective action against the impairment of the material properties by light, oxygen and heat. For turbine fuels (jet fuels) in particular, which are exposed to extreme thermal stress during and before the combustion operation in turbines, for example in aviation turbines, novel improved stabilizers are being sought. In the turbines, these should simultaneously also reduce deposits in the fuel circuit and in the combustion system by virtue of their mode of action as antioxidants and/or dispersants.

It was therefore an object of the invention to provide stabilizers with an improved stabilization of inanimate organic material, especially of mineral oil products and fuels, in particular of turbine fuel, against the action of light, oxygen and heat.

Accordingly, the use of tetrahydrobenzoxazines of the general formula I

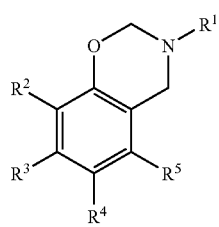

(I)

in which the substituent $R^1$ represents a hydrocarbyl radical which has from 1 to 3000 carbon atoms and may be interrupted by one or more heteroatoms from the group of O and S and/or by one or more $NR^6$ moieties, where $R^6$ represents a hydrogen atom or a $C_1$- to $C_4$-alkyl radical, and the substituents $R^2$, $R^3$, $R^4$ and $R^5$ are each independently hydrogen atoms, hydroxyl groups or hydrocarbyl radicals which have in each case from 1 to 3000 carbon atoms and may be interrupted by one or more heteroatoms from the group of O and S and/or by one or more $NR^6$ moieties, where the substituent $R^4$ may also be a radical of the formula Y

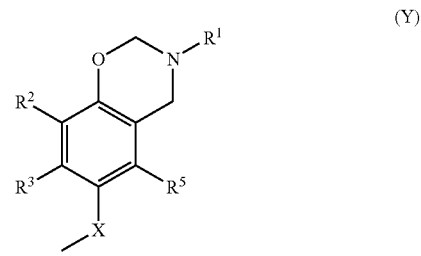

(Y)

in which the substituents $R^1$, $R^2$, $R^3$ and $R^5$ are each as defined above and the substituent X is a hydrocarbon bridging element which consists of one or more isobutene units or comprises one or more isobutene units, or where the substituent $R^4$ may also be a radical of the formula Z or Z'

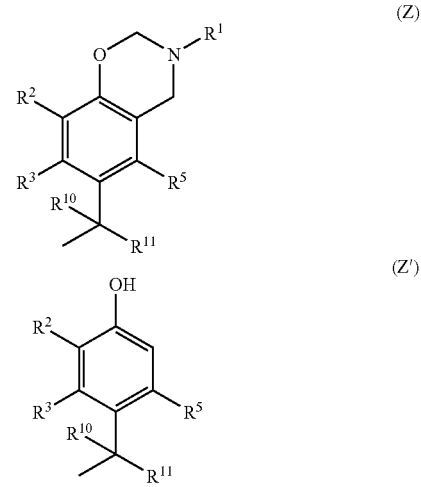

(Z)

(Z')

in which the substituents $R^1$, $R^2$, $R^3$ and $R^5$ are each as defined above and the substituents $R^{10}$ and $R^{11}$ may be the same or different and represent hydrogen or a $C_1$- to $C_{10}$-alkyl radical, and in which the substituents $R^2$ and $R^3$ or $R^3$ and $R^4$ or $R^4$ and $R^5$, together with the part-structure —O—CH$_2$—NR$^7$—CH$_2$— attached to the benzene ring, may also form a second tetrahydrooxazine ring, or the substituents $R^2$ and $R^3$ and $R^4$ and $R^5$, together with the part-structures —O—CH$_2$—NR$^7$—CH$_2$— and —O—CH$_2$—NR$^8$—CH$_2$— attached to the benzene ring, may also form a second and a third tetrahydrooxazine ring, where $R^7$ and $R^8$ are each independently hydrocarbyl radicals which have in each case from 1 to 3000 carbon atoms and may be interrupted by one or more heteroatoms from the group of O and S and/or by one or more $NR^6$ moieties, with the proviso that at least one of the substituents $R^1$, $R^2$, $R^3$, $R^4$, $R^5$, $R^7$ or $R^8$ has from 4 to 3000 carbon atoms and the remaining substituents from the group of $R^1$, $R^2$, $R^3$, $R^4$, $R^5$, $R^7$ and $R^8$, when they are hydrocarbyl radicals, each have from 1 to 20 carbon atoms, as stabilizers for stabilizing inanimate organic material against the action of light, oxygen and heat has been found.

Tetrahydrobenzoxazines are known in principle as additives for fuel and lubricant compositions. For instance, WO 01/25293 (3) and WO 01/25294 (4) disclose tetrahydrobenzoxazines with relatively long-chain radicals such as polyisobutenyl radicals which are situated as substituents on the benzene ring as gasoline fuel detergents which clean the valves and keep them clean. In the preparation processes disclosed in (3) and (4), these tetrahydrobenzoxazines are obtained as mixtures with the corresponding open-chain Mannich adducts of the parent phenol and also used thus in the gasoline fuels.

The preparation of tetrahydrobenzoxazines with short-chain substituents which are suitable, for example, as crop protection compositions, composed of 4-alkylphenols and an adduct of, for example, 1 mole of cyclohexylamine and 2 moles of formaldehyde or paraformaldehyde in methanol or ethanol as a solvent is described in U.S. Pat. No. 2,806,031 (5) and U.S. Pat. No. 3,132,960 (6).

The structural peculiarity of the tetrahydrobenzoxazines I to be used in accordance with the invention is that they comprise at least one relatively long-chain hydrocarbyl radical having from 4 to 3000 carbon atoms as one of the substituents $R^1$, $R^2$, $R^3$, $R^4$, $R^5$, $R^7$ or $R^8$, either on the benzene ring or on an oxazine ring. In a preferred embodiment, this relatively long-chain hydrocarbyl radical having from 4 to 3000 carbon atoms is a polyisobutenyl radical. In a further preferred embodiment, the relatively long-chain hydrocarbyl radical may also be a $C_{16}$- to $C_{20}$-alkyl or -alkenyl radical. In particular, this relatively long-chain hydrocarbyl radical, which is preferably a polyisobutenyl radical or a $C_{16}$- to $C_{20}$-alkyl or -alkenyl radical, is situated on an oxazine ring, i.e. it occurs as substituent $R^1$ or $R^7$ or $R^8$. This relatively long-chain hydrocarbyl radical, which is preferably a polyisobutenyl radical or a $C_{16}$- to $C_{20}$-alkyl or -alkenyl radical, is preferably also situated on the benzene ring as substituent $R^2$ or $R^4$. This relatively long-chain hydrocarbyl radical, which is preferably a polyisobutenyl radical or a $C_{16}$- to $C_{20}$-alkyl or -alkenyl radical, comprises preferably from 16 to 3000, especially from 20 to 1000, in particular from 25 to 500, most preferably from 30 to 250 carbon atoms. In the case of polyisobutenyl radicals, they preferably have number-average molecular weights $M_n$ of from 200 to 40 000, preferably from 500 to 15 000, especially from 700 to 7000, in particular from 900 to 3000, most preferably from 900 to 1100.

Suitable $C_{16}$- to $C_{20}$-alkyl or -alkenyl radicals are appropriately the radicals of corresponding saturated or unsaturated fatty alcohols having from 16 to 20 carbon atoms. Mention should be made here in particular of n-hexadecyl (palmityl), n-octadecyl (stearyl), n-eicosyl, oleyl, linolyl and linolenyl, which usually occur as technical mixtures with one another owing to their natural origin.

The relatively long-chain hydrocarbyl radical having from 4 to 3000 carbon atoms mentioned may also be present in the tetrahydrobenzoxazines I more than once, for example twice or three times. When it occurs twice, this relatively long-chain hydrocarbyl radical, which is preferably a polyisobutenyl radical and/or a $C_{16}$- to $C_{20}$-alkyl or -alkenyl radical, occurs, for example, as substituent $R^1$ and $R^4$ or $R^1$ and $R^7$.

In a preferred embodiment, one or two polyisobutenyl radicals having a number-average molecular weight $M_n$ of from 200 to 40 000 occur in the molecule as substituents $R^1$ and/or $R^2$ and/or $R^4$ and/or $R^7$ and/or $R^8$.

The remaining substituents from the group of $R^1$, $R^2$, $R^3$, $R^4$, $R^5$, $R^7$ and $R^8$ which are not substituents having from 4 to 3000 carbon atoms or polyisobutenyl radicals having a number-average molecular weight $M_n$ of from 200 to 40 000 each independently represent hydrogen atoms, hydroxyl groups or, when they are hydrocarbyl radicals, usually relatively short-chain hydrocarbyl radicals having from 1 to 20, preferably from 1 to 12, in particular from 1 to 8, most preferably linear or branched $C_1$- to $C_4$-alkyl radicals. Typical examples of the latter are methyl, ethyl, n-propyl, isopropyl, n-butyl, 2-butyl, sec-butyl and tert-butyl. In this context, very particular preference is given to methyl radicals and tert-butyl radicals.

Tetrahydrobenzoxazines I to be used with preference in accordance with the invention are also those in which the substituents $R^2$ and/or $R^4$, when they are relatively short-chain hydrocarbyl radicals, represent linear or branched $C_1$- to $C_4$-alkyl radicals, especially methyl radicals and/or tert-butyl radicals. Of course, such substitution patterns are only possible for tetrahydrobenzoxazines having a total of one or two tetrahydrooxazine ring systems.

In the radical of the formula Y, the substituent X denotes a hydrocarbon bridging element which consists of one or more, preferably from 4 to 800, especially from 10 to 300, in particular from 12 to 100 isobutene units, or comprises one or more, preferably from 4 to 800, especially from 10 to 300, in particular from 12 to 100 isobutene units. When X consists of isobutene units, it is attached generally via the α- and the ω-carbon atom. When X comprises further hydrocarbon structural units, they are preferably initiator molecule structural units arranged in the middle, such as aromatic ring systems, for example o-, m- or p-phenylene units, and/or hydrocarbon structural units with functional groups for attachment, for example o-, m- or p-hydroxyphenyl groups, as the chain conclusion at both ends. Such telechelic polyisobutene systems underlying the substituents X and their preparation are described, for example, in U.S. Pat. No. 4,429,099 (7).

In the radical of the formula Z or Z', the substituents $R^{10}$ and $R^{11}$ preferably represent hydrogen and/or linear or branched $C_1$- to $C_4$-alkyl radicals, in particular methyl radicals. The compound I having a Z or Z' radical, in which $R^{10}=R^{11}$=methyl, derives from bisphenol A [2,2-bis(4-hydroxyphenyl)propane]. As a result of the preparation, compounds I having a Z radical and compounds I having the corresponding Z' radical may also be present as mixtures.

Hydrocarbyl radicals having from 1 to 3000 or from 4 to 3000 carbon atoms for the substituents $R^1$, $R^2$, $R^3$, $R^4$, $R^5$, $R^7$ and $R^8$ should be understood here to mean pure hydrocarbon radicals of any structure, which, by definition, may also be interrupted by one or more heteroatoms from the group of O and S and/or by one or more $NR^6$ moieties. In particular, hydrocarbyl radicals are alkyl, alkenyl, cycloalkyl, aryl, alkylaryl, alkenylaryl or arylalkyl radicals.

Interruptions in the hydrocarbyl radical by $NR^6$ moieties also mean those radicals in which the $NR^6$ moieties have been inserted formally into a C—H bond at the end, i.e., for example, substituents $R^1$, $R^2$, $R^3$, $R^4$, $R^5$, $R^7$ or $R^8$ with an $NH_2$ end group. Such hydrocarbyl radicals derive, for example, from polyamines such as ethylenediamine, diethylenetriamine, triethylenetetramine, tetraethylenepentamine, etc., in which one of the terminal nitrogen atoms is the nitrogen atom in the oxazine ring.

The term "alkyl" comprises straight-chain and branched alkyl groups. Examples of the alkyl groups are, in addition to the methyl, ethyl, n-propyl, isopropyl, n-butyl, 2-butyl, sec-butyl and tert-butyl radicals, in particular also n-pentyl, 2-pentyl, 2-methylbutyl, 3-methylbutyl, 1,2-dimethylpropyl, 1,1-dimethylpropyl, 2,2-dimethylpropyl, 1-ethyl-propyl, n-hexyl, 2-hexyl, 2-methylpentyl, 3-methylpentyl, 4-methylpentyl, 1,2-dimethyl-butyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-dodecyl, n-tridecyl, isotridecyl, n-tetradecyl (myristyl), n-hexadecyl (palmityl), n-octadecyl (stearyl), and n-eicosyl.

Examples of alkenyl radicals are vinyl, 1-propenyl, 2-propenyl, oleyl, linolyl and linolenyl.

Examples of cycloalkyl radicals are $C_5$- to $C_7$-cycloalkyl groups such as cyclopentyl, cyclohexyl and cycloheptyl, which may also be substituted by alkyl groups, for example methyl radicals.

The term "aryl" comprises monocyclic, bicyclic, tricyclic and higher polycyclic aromatic hydrocarbon radicals. In the case of substitution by the alkyl and/or alkenyl radicals, for example those mentioned above, to give alkylaryl or alkenylaryl radicals, these aryl radicals may also bear 1, 2, 3, 4 or 5, preferably 1, 2 or 3 substituents. Typical examples are phenyl, tolyl, xylyl, mesityl, naphthyl, fluorenyl, anthracenyl, phenanthrenyl, naphthacenyl and styryl. A typical example of an arylalkyl radical is benzyl.

When the relatively long-chain hydrocarbyl radical having from 4 to 3000 carbon atoms is a polyisobutenyl radical, it may be based in principle on any common and commercially available polyisobutene, which is introduced in a suitable manner into the synthesis of the tetrahydrobenzoxazines 1. Such a polyisobutene preferably has a number-average molecular weight $M_n$ of at least 200. Preference is given to polyisobutenes having a number-average molecular weight $M_n$ in the range from 200 to 40 000, more preferably from 500 to 15 000, in particular from 700 to 7000, especially from 900 to 3000 and most preferably from 900 to 1100. In the context of the present invention, the term "polyisobutene" also includes oligomeric isobutenes such as dimeric, trimeric, tetrameric, pentameric, hexameric and heptameric isobutene.

The polyisobutenyl radicals incorporated into the tetrahydrobenzoxazines I used in accordance with the invention preferably derive from so-called "high-reactivity" polyisobutene. "High-reactivity" polyisobutenes differ from the "low-reactivity" polyisobutenes by the content of terminal double bonds. Thus, high-reactivity polyisobutenes comprise at least 50 mol % of terminal double bonds based on the total number of polyisobutene macromolecules. Particular preference is given to polyisobutenes having at least 60 mol % and especially having at least 80 mol % of terminal double bonds based on the total number of polyisobutene macromolecules. The terminal double bonds may either be vinyl double bonds [—CH=C(CH$_3$)$_2$] (β-olefin) or vinylidene double bonds [—CH—C(=CH$_2$)—CH$_3$] (α-olefin). The substantially homopolymeric polyisobutene radicals also have uniform polymer backbones. Among these, preference is given in the context of the present invention to those polyisobutene systems which are formed to an extent of at least 85% by weight, preferably to an extent of at least 90% by weight and more preferably to an extent of at least 95% by weight from isobutene units of the repeat unit [—CH$_2$C(CH$_3$)$_2$—].

A further preferred feature of the polyisobutenes which can underly the tetrahydrobenzoxazines I used in accordance with the invention is that they are terminated by a tert-butyl group [—CH$_2$C(CH$_3$)$_3$] to an extent of at least 15% by weight, especially to an extent of at least 50% by weight, in particular to an extent of at least 80% by weight.

Moreover, the polyisobutenes preferably serving as the basis of the tetrahydrobenzoxazines I used in accordance with the invention preferably have a polydispersity index (PDI) of from 1.05 to 10, preferably from 1.05 to 3.0, in particular from 1.05 to 2.0. Polydispersity is understood to mean the quotient of weight-average molecular weight $M_w$ and number-average molecular weight $M_n$ (PDI=$M_w$/$M_n$).

In the context of the present invention, the polyisobutenes preferably serving as the basis of the tetrahydrobenzoxazines I used in accordance with the invention are also understood to mean all polymers which are obtainable by cationic polymerization and comprise, in copolymerized form, preferably at least 60% by weight of isobutene, more preferably at least 80% by weight, in particular at least 90% by weight and especially at least 95% by weight of isobutene. In addition, the polyisobutenes may comprise, in copolymerized form, further butene isomers such as 1- or 2-butene, and also different olefinically unsaturated monomers which are copolymerizable with isobutene under cationic polymerization conditions.

Suitable isobutene feedstocks for the preparation of polyisobutenes which can serve as the basis of the tetrahydrobenzoxazines I used in accordance with the invention are accordingly both isobutene itself and isobutenic $C_4$ hydrocarbon streams, for example $C_4$ raffinates, $C_4$ cuts from isobutene dehydrogenation, $C_4$ cuts from steamcrackers, FCC crackers (FCC: Fluid Catalyzed Cracking), provided that they have been substantially freed of 1,3-butadiene present therein. Particularly suitable $C_4$ hydrocarbon streams comprise generally less than 500 ppm, preferably less than 200 ppm of butadiene. When $C_4$ cuts are used as the starting material, the hydrocarbons other than isobutene assume the role of an inert solvent.

Useful monomers copolymerizable with isobutene include vinylaromatics such as styrene and α-methylstyrene, $C_1$-$C_4$-alkylstyrenes such as 2-, 3- and 4-methylstyrene, and also 4-tert-butylstyrene, isoolefins having from 5 to 10 carbon atoms such as 2-methylbutene-1,2-methylpentene-1,2-methylhexene-1,2-ethylpentene-1,2-ethylhexene-1 and 2-propylheptene-1.

Typical polyisobutenes which may serve as the basis of the tetrahydrobenzoxazines I used in accordance with the invention are, for example, the Glissopal® brands from BASF Aktiengesellschaft, for example Glissopal 550, Glissopal 1000 and Glissopal 2300, and also the Oppanol® brands from BASF Aktiengesellschaft, for example Oppanol B10, B12 and B15.

Examples of tetrahydrobenzoxazines I typical in the context of the present invention, with a tetrahydrooxazine ring on the benzene ring, are the following, where "PIB" represents a polyisobutenyl radical derived from a high-reactivity polyisobutene ($M_n$ 1000) and "PIB*" is a polyisobutylene bridging element derived from a high-reactivity polyisobutene ($M_n$ 870):

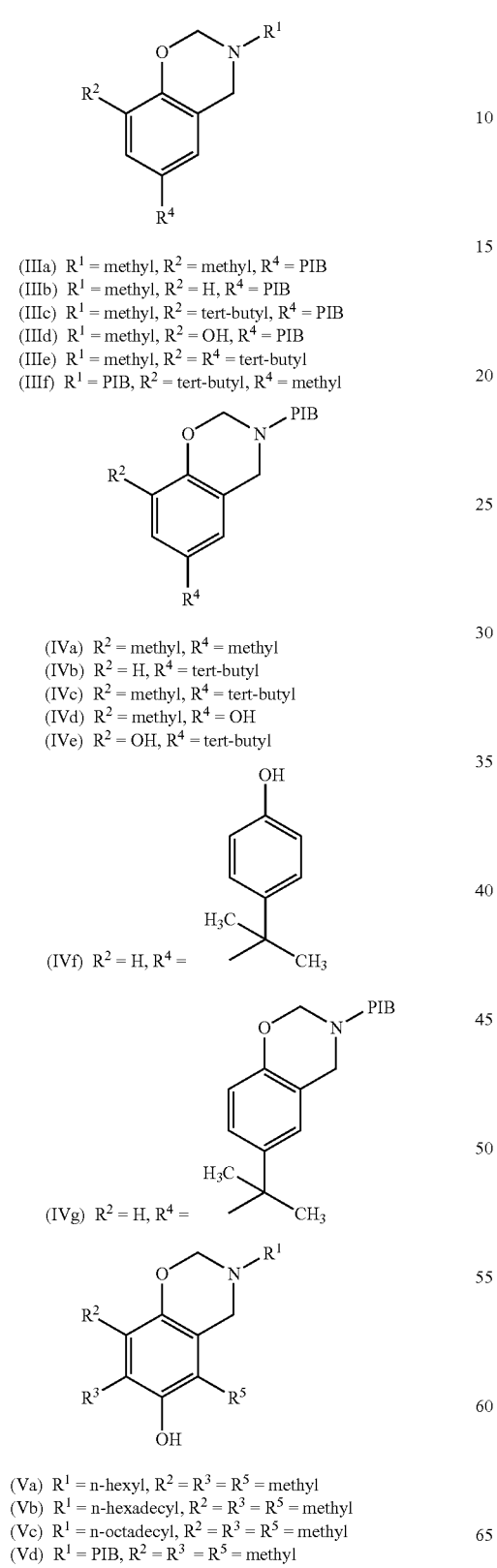

(IIIa) $R^1$ = methyl, $R^2$ = methyl, $R^4$ = PIB
(IIIb) $R^1$ = methyl, $R^2$ = H, $R^4$ = PIB
(IIIc) $R^1$ = methyl, $R^2$ = tert-butyl, $R^4$ = PIB
(IIId) $R^1$ = methyl, $R^2$ = OH, $R^4$ = PIB
(IIIe) $R^1$ = methyl, $R^2$ = $R^4$ = tert-butyl
(IIIf) $R^1$ = PIB, $R^2$ = tert-butyl, $R^4$ = methyl (IVa) $R^2$ = methyl, $R^4$ = methyl
(IVb) $R^2$ = H, $R^4$ = tert-butyl
(IVc) $R^2$ = methyl, $R^4$ = tert-butyl
(IVd) $R^2$ = methyl, $R^4$ = OH
(IVe) $R^2$ = OH, $R^4$ = tert-butyl (IVf) $R^2$ = H, $R^4$ =

(IVg) $R^2$ = H, $R^4$ =

(Va) $R^1$ = n-hexyl, $R^2$ = $R^3$ = $R^5$ = methyl
(Vb) $R^1$ = n-hexadecyl, $R^2$ = $R^3$ = $R^5$ = methyl
(Vc) $R^1$ = n-octadecyl, $R^2$ = $R^3$ = $R^5$ = methyl
(Vd) $R^1$ = PIB, $R^2$ = $R^3$ = $R^5$ = methyl

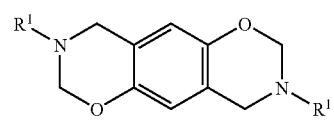

(VIa) $R^1$ = n-hexadecyl
(VIa) $R^1$ = n-octadecyl

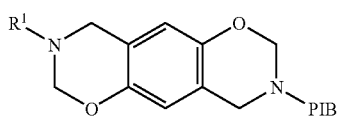

(VIIa) $R^1$ = methyl
(VIIb) $R^1$ = n-octadecyl

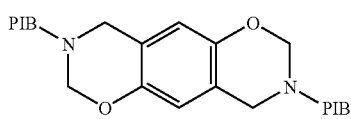

(VII)

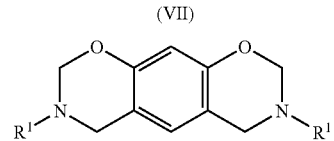

(IXa) $R^1$ = n-hexadecyl
(IXb) $R^1$ = n-octadecyl

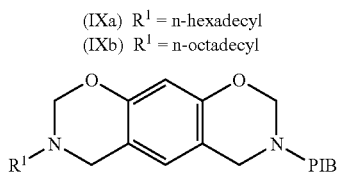

(Xa) $R^1$ = methyl
(Xb) $R^1$ = n-octadecyl

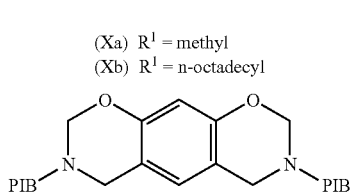

(XI)

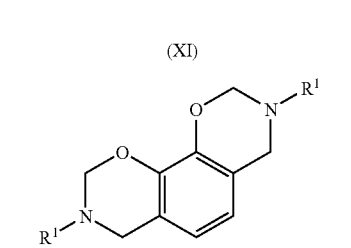

(XIIa) $R^1$ = n-hexadecyl
(XIIb) $R^1$ = n-octadecyl

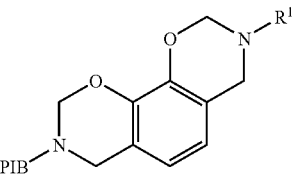

(XIIIa) $R^1$ = methyl
(XIIIb) $R^1$ = n-octadecyl

-continued

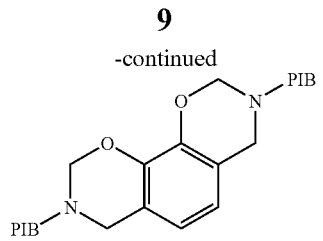

(XIV)

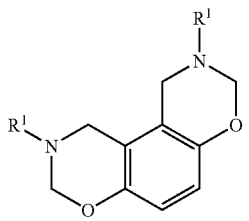

(XVa) R¹ = n-hexadecyl
(XVb) R¹ = n-octadecyl

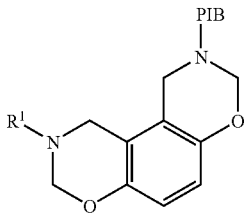

(XVIa) R¹ = methyl
(XVIb) R¹ = n-octadecyl

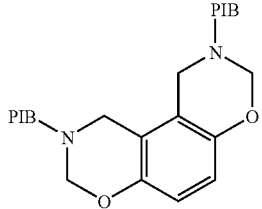

(XVII)

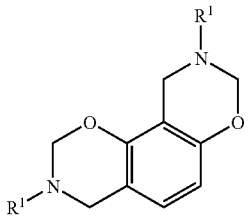

(XVIIIa) R¹ = n-hexadecyl
(XVIIIb) R¹ = n-octadecyl

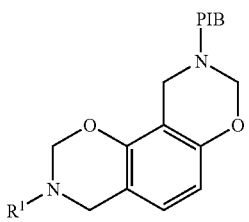

(XIXa) R¹ = methyl
(XIXb) R¹ = n-octadecyl

-continued

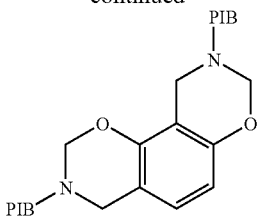

(XX)

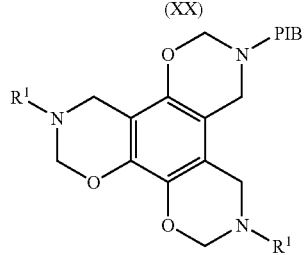

(XXIa) R¹ = methyl
(XXIb) R¹ = octadecyl

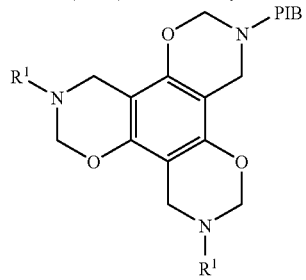

(XXIIa) R¹ = methyl
(XXIIb) R¹ = n-octadecyl

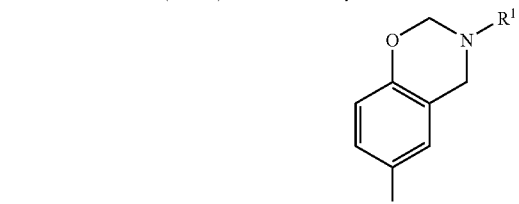

(XXIIIa) R¹ = Methyl

As a result of the preparation, it is also possible for mixtures in each case of the compounds VIa+XVa, VIb+XVb, VIIa+XVIIa, VIIb+XVIb, VIII+XVII, IXa+XVIIIa, IXb+XVIIIb, Xa+XIXa, Xb+XIXb or XI+XX to occur, and to be used in this form in accordance with the invention.

In a preferred embodiment, tetrahydrobenzoxazines I in which the substituents R³ and R⁴ or R⁴ and R⁵, together with a part-structure —O—CH₂—NR⁷—CH₂— oxygen-attached via the substituent R⁴, form a second tetrahydrooxazine ring are used for the present invention. Examples thereof are the above-listed compounds VI to XX.

The tetrahydrobenzoxazines I described are used in accordance with the present invention as stabilizers for stabilizing inanimate organic material against the action of light, oxygen and heat. This is understood to mean in particular their mode of action as antioxidants in the conventional sense. To this end, the compounds are incorporated into the material to be stabilized during or after its production and distributed as homogeneously as possible. The concentration of these compounds in the organic material to be stabilized is generally from 0.0001 to 5% by weight, preferably from 0.001 to 5% by weight, in particular form 0.01 to 2% by weight, especially from 0.05 to 1% by weight, based on the organic material.

Inanimate organic material is understood to mean, for example, cosmetic preparations such as ointments and lotions, medicament formulations such as pills and suppositories, photographic recording materials, especially photographic emulsions, paints and plastics. They further include especially mineral oil products and fuels, for example diesel fuel, gasoline fuel, turbine fuel, motor or lubricant oils, gearbox oils and lubricant greases.

Examples of plastics which may be stabilized by the tetrahydrobenzoxazines I described include:

polymers of mono- or diolefins, such as low- or high-density polyethylene, polypropylene, linear polybutene-1, polyisoprene, polybutadiene, and also copolymers of mono- or diolefins or mixtures of the polymers mentioned;

polystyrene and copolymers of styrene or α-methylstyrene with dienes and/or acrylic derivatives, for example styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS); halogen-containing polymers, for example polyvinyl chloride, polyvinyl fluoride, polyvinylidene fluoride and their copolymers;

polymers which derive from α,β-unsaturated acids and their derivatives, such as polyacrylates, polymethacrylates, polyacrylamides and polyacrylonitriles;

polymers which derive from unsaturated alcohols and amines or from their acyl derivatives or acetals, for example polyvinyl alcohol and polyvinyl acetate;

polyurethanes, especially thermoplastic polyurethanes, polyamides, polyureas, polyphenylene ethers, polyesters, polycarbonates, polysulfones, polyethersulfones and polyetherketones.

The paints which can be stabilized with the tetrahydrobenzoxazines I described include coatings such as alkyd resin coating, dispersion coatings, epoxy resin coatings, polyurethane coatings, acrylic resin coatings and cellulose nitrate coatings, or varnishes such as wood protection varnishes.

The tetrahydrobenzoxazines I described are suitable in a particularly advantageous manner as stabilizers in turbine fuels (jet fuels). This is also understood to mean their mode of action as antioxidants in the conventional sense. In particular, by virtue of their mode of action as stabilizers, they serve to improve the thermal stability of turbine fuels. Moreover, especially also by virtue of their action as stabilizers, i.e. in their property as dispersants, they prevent deposits in the fuel system and/or combustion system of turbines. Turbine fuels are used in particular for operating aviation turbines.

The present invention further provides a turbine fuel composition which comprises a turbine fuel (jet fuel) and at least one of the tetrahydrobenzoxazines I described.

The inventive turbine fuel composition comprises a majority of a liquid turbine fuel, which is, for example, a turbine fuel customary in civilian or military aviation. These include, for example, fuels of the designation Jet Fuel A, Jet Fuel A-1, Jet Fuel B, Jet Fuel JP-4, JP-5, JP-7, JP-8 and JP-8+100. Jet A and Jet A-1 are commercially available turbine fuel specifications based on kerosene. The accompanying standards are ASTM D 1655 and DEF STAN 91-91. Jet B is a more highly cut fuel based on naphtha and kerosene fractions. JP-4 is equivalent to Jet B. JP-5, JP-7, JP-8 and JP-8+100 are military turbine fuels, as used, for example, by the Marines and Air Force. Some of these standards relate to formulations which already comprise further additives such as corrosion inhibitors, icing inhibitors, static dissipaters, etc.

The tetrahydrobenzoxazines I described may be added to the turbine fuel or to the turbine fuel composition individually, as mixtures and, if appropriate, in combination with further additives known per se.

Suitable additives which may be present in the inventive turbine fuel composition comprise typically detergents, corrosion inhibitors, further antioxidants such as sterically hindered tert-butylphenols, n-butylphenylenediamines or N,N'-diphenylamine and derivatives thereof, metal deactivators such as N,N'-disalicylidene-1,2-diamino-propane, solubilizers, antistats such as Stadis 450, biocides, anti-icing agents such as diethylene glycol methyl ether, and also mixtures of the additives mentioned.

Additives preferred in the context of the present invention are the specific compound classes (A), (B) and (C) detailed below:

Preferred additives (A) are compounds which derive from succinic anhydride and have long-chain hydrocarbon radicals having generally from 15 to 700, in particular from 30 to 200 carbon atoms. These compounds may have further functional groups which are preferably selected from hydroxyl, amino, amido and/or imido groups. Preferred additives are the corresponding derivatives of polyalkenylsuccinic anhydride which are obtainable, for example, by reacting polyalkenes with maleic anhydride by a thermal route or via the chlorinated hydrocarbons. The number-average molecular weight of the long-chain hydrocarbon radicals is preferably in a range from about 200 to 10 000, more preferably from 400 to 5000, in particular from 600 to 3000 and especially from 650 to 2000. These long-chain hydrocarbon radicals preferably derive from conventional polyisobutenes and especially from the aforementioned reactive polyisobutenes. Of particular interest as additives (A) are the derivatives of polyalkenylsuccinic anhydrides with ammonia, monoamines, polyamines, monoalcohols and polyols. Polyamines preferred for derivatization comprise ethylenediamine, diethylenetriamine, triethylenetetramine, tetraethylenepentamine, propylenediamine, etc. Suitable alcohols comprise monohydric alcohols such as ethanol, allyl alcohol, dodecanol and benzyl alcohol, polyhydric alcohols such as ethylene glycol, diethylene glycol, propylene glycol, 1,2-butanediol, neopentyl glycol, glycerol, trimethylolpropane, erythritol, pentaerythritol, mannitol and sorbitol.

Succinic anhydride derivatives (A) suitable as additives are described, for example, in U.S. Pat. Nos. 3,522,179, 4,234, 435, 4,849,572, 4,904,401, 5,569,644 and 6,165,235, which is fully incorporated here by reference.

Preferred additives (B) are polyalkenylthiophosphonate esters. The polyalkenyl radical of these esters preferably has a number-average molecular weight in the range from about 300 to 5000, more preferably from 400 to 2000 and in particular form 500 to 1500. The polyalkenyl radical derives preferably from polyolefins as have already been described as long-chain hydrocarbon radical for component (A). They are especially polyalkenyl radicals which derive from conventional or reactive polyisobutenes. Suitable processes for preparing suitable polyalkenylthiophosphonate esters by reacting a polyolefin with a thiophosphorylating agent are described, for example, in U.S. Pat. No. 5,725,611, which is incorporated here by reference.

Preferred additives (C) are Mannich adducts. Such additives are obtained in principle by Mannich reaction of aromatic hydroxyl compounds, especially phenol and phenol derivatives, with aldehydes and mono- or polyamines. They are preferably the reaction products of polyisobutene-substituted phenols with formaldehyde and mono- or polyamines such as ethylenediamine, diethylenetriamine, triethylenetetramine, tetraethylenepentamine, dimethylaminopropylamine, etc. Suitable Mannich adducts and processes for their preparation are described, for example, in U.S. Pat. No. 5,876,468, EP-A 831 141, EP-A 1 233 990 and EP-A 1 226 188, which are incorporated here by reference.

The inventive turbine fuel composition comprises the tetrahydrobenzoxazines I described in an amount of typically from 0.0001 to 1% by weight, preferably from 0.001 to 0.5% by weight, especially from 0.01 to 0.2% by weight and in particular from 0.01 to 0.1% by weight, based on the total amount of the turbine fuel composition.

The additives (A) to (C) and, if appropriate, further additives from those mentioned above may typically each be used in amounts of in each case from 0.0001 to 1% by weight, preferably from 0.001 to 0.6% by weight and in particular from 0.0015 to 0.4% by weight, based on the total amount of the turbine fuel composition.

The present invention further provides an additive concentrate for turbine fuels (jet fuels) which comprises at least one of the tetrahydrobenzoxazines I described and, if appropriate, at least one diluent and, if appropriate, at least one further additive which is preferably selected from those described above. In a preferred embodiment, the inventive additive concentrate, and hence also the inventive turbine fuel composition, comprises one or more additives from the group of (A), (B) and (C), especially also mixtures thereof such as (A)+(B), (A)+(C), (B)+(C) and (A)+(B)+(C).

Suitable diluents are, for example, fractions obtained in crude oil processing, such as kerosene, naphtha or brightstock. Also suitable are aromatic and aliphatic hydrocarbons such as Solvent Naphtha heavy, Solvesso® or Shellsol®, and also mixtures of these solvents and diluents.

The tetrahydrobenzoxazines I described are present in the inventive additive concentrate preferably in an amount of from 0.1 to 100% by weight, more preferably from 1 to 80% by weight and in particular from 10 to 70% by weight, based on the total weight of the concentrate.

The present invention also provides a process for preparing tetrahydrobenzoxazines 1, which comprises reacting an appropriately substituted phenol, pyrocatechol, resorcinol, hydroquinone, phloroglucinol or hydroxyhydroquinone with a reagent, preformed from one mole of a primary amine of the formula $R^1$—$NH_2$ or $R^7$—$NH_2$ or $R^8$—$NH_2$, two moles of formaldehyde or of a formaldehyde-releasing substance and two moles of a linear or branched $C_1$- to $C_8$-alcohol of the formula $R^9$—OH, of the general formula II

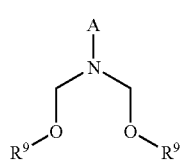

(II)

in which A is the substituents $R^1$, $R^7$ or $R^8$ which are each as defined above, under suitable conditions. Depending on the desired number of tetrahydrooxazine rings and of hydroxyl groups present on the benzene ring, the aromatic hydroxyl compound can be reacted here with 1, 2 or 3 equivalents of reagent II. The resulting tetrahydrobenzoxazine 1, as described above, has at least one hydrocarbyl radical which has from 4 to 3000 carbon atoms and may be interrupted by one or more heteroatoms from the group of O and S and/or by one or more $NR^6$ moieties.

Suitable linear or branched $C_1$- to $C_8$-alcohols of the formula $R^9$—OH are in particular linear or branched $C_1$- to $C_8$-alkanols such as methanol, ethanol, isopropanol, isobutanol and sec-butanol.

Suitable conditions for the reaction of the aromatic hydroxyl compounds with the reagent II are, for example, temperatures of from 0 to 130° C., in particular from 20 to 100° C. It is appropriate to work in an inert organic solvent, especially an aromatic hydrocarbon such as toluene or xylene.

The reagent II is typically prepared from the feedstocks specified by distilling off the water freed in the course of its formation. A suitable method for this purpose is, for example, heating in a water-separating inert organic solvent, especially an aromatic hydrocarbon such as toluene or xylene. However, the water released can in principle also remain in the reagent II where it does not disrupt the further reactions. The formaldehyde-releasing substance used may, for example, be paraformaldehyde.

The preparation process according to the invention has the advantage that the desired tetrahydrobenzoxazine I is obtained in high yield, i.e. substantially without undesired by-products or at least in highly enriched form.

In some cases, the desired tetrahydrobenzoxazine I can be obtained in appropriate purity even without preceding provision of the reagent II, by direct reaction of the appropriately substituted aromatic hydroxyl compound with one mole of a primary amine of the formula $R^1$—$NH_2$ or $R^7$—$NH_2$ or $R^8$—$NH_2$ and two moles of formaldehyde or of a formaldehyde-releasing substance (per hydroxyl group to be converted), the reaction being carried out, if appropriate, in a suitable solvent such as an alcohol, for example a linear or branched $C_1$- to $C_8$-alcohol of the formula $R^9$—OH. In this method, however, there is the risk in principle that, depending on the reactant structure, stoichiometry and reaction conditions, not inconsiderable amounts of undesired open-chain conventional Mannich adducts can form from aromatic hydroxyl compound, amine and formaldehyde.

Since some of the tetrahydrobenzoxazines I described are novel substances, these novel substances themselves also form part of the subject matter of the present invention.

Tetrahydrobenzoxazines I in which the relatively long-chain hydrocarbyl radical(s) having in each case from 20 to 3000 carbon atoms are present as substituents on the nitrogen atoms of the tetrahydrooxazine rings are novel. The present invention therefore also provides tetrahydrobenzoxazines of the general formula Ia

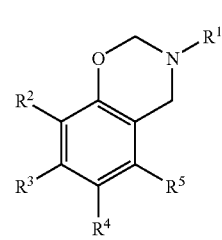

(Ia)

in which the substituent $R^1$ represents a hydrocarbyl radical which has from 1 to 3000 carbon atoms and may be interrupted by one or more heteroatoms from the group of O and S and/or by one or more NR$^6$ moieties, where R$^6$ represents a hydrogen atom or a C$_1$- to C$_4$-alkyl radical, and the substituents R$^2$, R$^3$, R$^4$ and R$^5$ are each independently hydrogen atoms, hydroxyl groups or hydrocarbyl radicals which have in each case from 1 to 3000 carbon atoms and may be interrupted by one or more heteroatoms from the group of O and S and/or by one or more NR$^6$ moieties, where the substituent R$^4$ may also be a radical of the formula Y

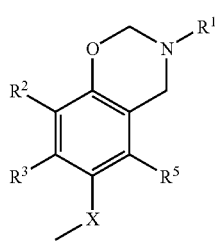
(Y)

in which the substituents R$^1$, R$^2$, R$^3$ and R$^5$ are each as defined above and the substituent X is a hydrocarbon bridging element which consists of one or more isobutene units or comprises one or more isobutene units, or where the substituent R$^4$ may also be a radical of the formula Z or Z'

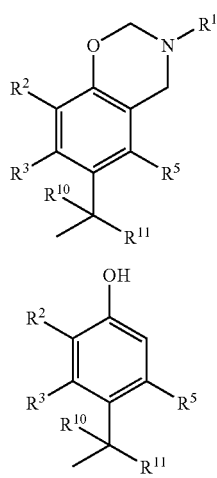
(Z)

(Z')

in which the substituents R$^1$, R$^2$, R$^3$ and R$^5$ are each as defined above and the substituents R$^{10}$ and R$^{11}$ may be the same or different and represent hydrogen or a C$_1$- to C$_{10}$-alkyl radical, and in which the substituents R$^2$ and R$^3$ or R$^3$ and R$^4$ or R$^4$ and R$^5$, together with the part-structure —O—CH$_2$—NR$^7$—CH$_2$— attached to the benzene ring, may also form a second tetrahydrooxazine ring, or the substituents R$^2$ and R$^3$ and R$^4$ and R$^5$, together with the part-structures —O—CH$_2$—NR$^7$—CH$_2$— and —O—CH$_2$—NR$^8$—CH$_2$— attached to the benzene ring, may also form a second and a third tetrahydrooxazine ring, where R$^7$ and R$^8$ are each independently hydrocarbyl radicals which have in each case from 1 to 3000 carbon atoms and may be interrupted by one or more heteroatoms from the group of O and S and/or by one or more NR$^6$ moieties, with the proviso that at least one of the substituents R$^1$ or R$^7$ or R$^8$ has from 20 to 3000 carbon atoms and the remaining substituents from the group of R$^1$, R$^2$, R$^3$, R$^4$, R$^5$, R$^7$ and R$^8$, when they are hydrocarbyl radicals, each have from 1 to 20 carbon atoms.

Tetrahydrobenzoxazines I having hydroxyl groups which are in the 2- and/or 4-position on the benzene ring, and having relatively long-chain hydrocarbyl radicals having in each case from 4 to 3000 carbon atoms as substituents on the nitrogen atoms of the tetrahydrooxazine rings are novel. The present invention therefore also provides tetrahydrobenzoxazines of the general formula Ib

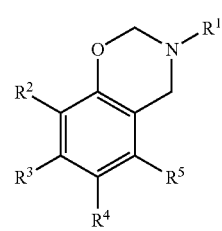
(Ib)

in which the substituent R$^1$ represents a hydrocarbyl radical which has from 1 to 3000 carbon atoms and may be interrupted by one or more heteroatoms from the group of O and S and/or by one or more NR$^6$ moieties, where R$^6$ represents a hydrogen atom or a C$_1$- to C$_4$-alkyl radical, and the substituents R$^2$, R$^3$, R$^4$ and R$^5$ are each independently hydrogen atoms, hydroxyl groups or hydrocarbyl radicals which have in each case from 1 to 3000 carbon atoms and may be interrupted by one or more heteroatoms from the group of O and S and/or by one or more NR$^6$ moieties, where the substituent R$^4$ may also be a radical of the formula Y

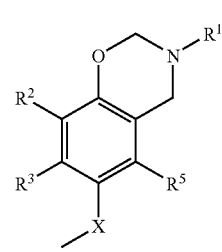
(Y)

in which the substituents R$^1$, R$^2$, R$^3$ and R$^5$ are each as defined above and the substituent X is a hydrocarbon bridging element which consists of one or more isobutene units or comprises one or more isobutene units, or where the substituent R$^4$ may also be a radical of the formula Z or Z'

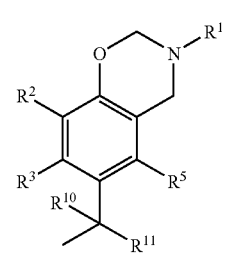
(Z)

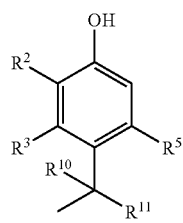

(Z')

in which the substituents $R^1$, $R^2$, $R^3$ and $R^5$ are each as defined above and the substituents $R^{10}$ and $R^{11}$ may be the same or different and represent hydrogen or a $C_1$- to $C_{10}$-alkyl radical, and in which the substituents $R^2$ and $R^3$ or $R^3$ and $R^4$ or $R^4$ and $R^5$, together with the part-structure —O—CH$_2$—NR$^7$—CH$_2$— attached to the benzene ring, may also form a second tetrahydrooxazine ring, where $R^7$ is a hydrocarbyl radical which has from 1 to 3000 carbon atoms and may be interrupted by one or more heteroatoms from the group of O and S and/or by one or more NR$^6$ moieties, with the proviso that at least one of the substituents $R^1$ or $R^7$ has from 4 to 3000 carbon atoms and the remaining substituents from the group of $R^1$, $R^2$, $R^3$, $R^4$, $R^5$ and $R^7$, when they are hydrocarbyl radicals, each have from 1 to 20 carbon atoms, and with the proviso that the substituents $R^2$ and/or $R^4$ are hydroxyl groups.

Tetrahydrobenzoxazines I having a tetrahydrooxazine ring in which the relatively long-chain hydrocarbyl radical(s) are certain polyisobutenyl radicals and/or certain alk(en)yl radicals and are in the 2- and/or 4-position on the benzene ring and the alkyl radical has from 1 to 4 carbon atoms on the nitrogen atom are novel. The present invention therefore also provides tetrahydrobenzoxazines of the general formula Ic

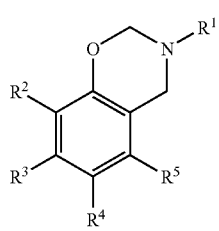

(Ic)

in which the substituent $R^1$ represents a $C_1$- to $C_4$-alkyl radical, the substituents $R^2$ and/or $R^4$ are each independently $C_{16}$- to $C_{20}$-alkyl or -alkenyl radicals and/or polyisobutenyl radicals having a number-average molecular weight $M_n$ of from 900 to 3000 and the substituents $R^3$ and $R^5$ are each hydrogen.

Tetrahydrobenzoxazines I which have a second tetrahydrooxazine ring or a second and a third tetrahydrooxazine ring on the benzene ring are novel. The present invention therefore also provides tetrahydrobenzoxazines of the general formula Id

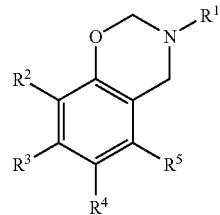

(Id)

in which the substituent $R^1$ represents a hydrocarbyl radical which has from 1 to 3000 carbon atoms and may be interrupted by one or more heteroatoms from the group of O and S and/or by one or more NR$^6$ moieties, where $R^6$ represents a hydrogen atom or a $C_1$- to $C_4$-alkyl radical, and the substituents $R^2$, $R^3$, $R^4$ and $R^1$ are each independently hydrogen atoms, hydroxyl groups or hydrocarbyl radicals which have in each case from 1 to 3000 carbon atoms and may be interrupted by one or more heteroatoms from the group of O and S and/or by one or more NR$^6$ moieties, where the substituent $R^4$ may also be a radical of the formula Y

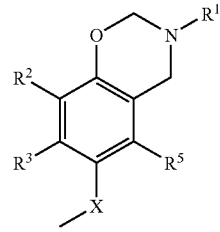

(Y)

in which the substituents $R^1$, $R^2$, $R^3$ and $R^5$ are each as defined above and the substituent X is a hydrocarbon bridging element which consists of one or more isobutene units or comprises one or more isobutene units, or where the substituent $R^4$ may also be a radical of the formula Z or Z'

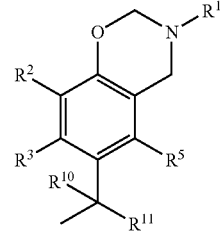

(Z)

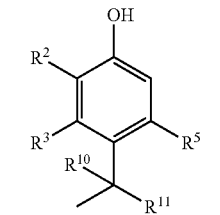

(Z')

in which the substituents $R^1$, $R^2$, $R^3$ and $R^5$ are each as defined above and the substituents $R^{10}$ and $R^{11}$ may be the same or different and represent hydrogen or a $C_1$- to $C_{10}$-alkyl radical, and in which the substituents $R^2$ and $R^3$ or $R^3$ and $R^4$ or $R^4$ and $R^5$, together with the part-structure —O—CH$_2$—NR$^7$—CH$_2$— attached to the benzene ring, may form a second tetrahydrooxazine ring, or the substituents $R^2$ and $R^3$ and $R^4$ and $R^5$, together with the part-structures —O—CH$_2$—NR$^7$—CH$_2$— and —O—CH$_2$—NR$^8$—CH$_2$— attached to the benzene ring, may form a second and a third tetrahydrooxazine ring, where $R^7$ and $R^8$ are each independently hydrocarbyl radicals which have in each case from 1 to 3000 carbon atoms and may be interrupted by one or more heteroatoms from the group of O and S and/or by one or more NR$^6$ moieties, with the proviso that at least one of the substituents $R^1$, $R^2$, $R^3$, $R^4$, $R^5$, $R^7$ or $R^8$ has from 4 to 3000 carbon atoms and the remaining substituents from the group of $R^1$, $R^2$, $R^3$, $R^4$, $R^5$, $R^7$ and $R^8$, when they are hydrocarbyl radicals, each have from 1 to 20 carbon atoms.

The invention will be illustrated in detail with reference to the nonlimiting examples which follow.

PREPARATION EXAMPLES

Example 1

N,N-Di(isobutoxymethyl)-N-methylamine (Reagent of the Formula II)

A 2 l four-neck flask with water separator was initially charged with 600 ml of isobutanol and 90 g of paraformaldehyde. 113 g of a 41% by weight aqueous methylamine solution were then added dropwise over 12 minutes, in the course of which the temperature rose to 44° C. After addition of 200 ml of toluene, the mixture was heated under vigorous reflux, in the course of which 126 ml of water separated out. Low boilers were distilled off on a rotary evaporator at 60° C. and 15 mbar. 244 g of product were obtained in the form of a light, clear liquid with amine-like odor.

$^1$H NMR (400 MHz, 16 scans, CDCl$_3$):
δ=4.23 ppm, 4H, CH$_3$—N[CH$_2$—O—CH$_2$—CH(CH$_3$)$_2$]$_2$
δ=3.17 ppm, 4H, CH$_3$—N[CH$_2$—O—CH$_2$—CH(CH$_3$)$_2$]$_2$
δ=2.55 ppm, 3H, CH$_3$—N[CH$_2$—O—CH$_2$—CH(CH$_3$)$_2$]$_2$
δ=1.83 ppm, 2H, CH$_3$—N[CH$_2$—O—CH$_2$—CH(CH$_3$)$_2$]$_2$
δ=0.91 ppm, 12H, CH$_3$—N[CH$_2$—O—CH$_2$—CH(CH$_3$)$_2$]$_2$ Example 2

Tetrahydrobenzoxazine of the Formula Vc

A 500 ml four-neck flask was initially charged with 30 g of paraformaldehyde at room temperature in 100 ml of isopropanol. 142 g of molten n-octadecylamine were added rapidly. The flask contents were heated to reflux and stirred under reflux for 30 minutes. 76 g of trimethylhydroquinone were added in 3 portions within 15 minutes. The mixture was stirred under reflux for 30 minutes. In the course of cooling to room temperature, a solid precipitated out and was filtered off with suction through a D3 suction filter. The filter residue was washed repeatedly with heptane. Subsequently, the residue was dried overnight in a vacuum drying cabinet at 50° C. and 100 mbar under nitrogen atmosphere. 186.4 g of product were obtained.

$^1$H NMR (400 MHz, 16 scans, CDCl$_3$):
δ=4.70 ppm, 2H, —CH$_2$—N(CH$_3$)—CH$_2$—O—
δ=3.82 ppm, 2H, —CH$_2$—N(CH$_3$)—CH$_2$—O—

Example 3

Tetrahydrobenzoxazines of the Formulae VIa+XVa

A 500 ml four-neck flask was initially charged with 30 g of paraformaldehyde at room temperature in 100 ml of isopropanol. 142 g of molten n-octadecylamine were added rapidly. The flask contents were heated to reflux and stirred under reflux for 30 minutes. 27.5 g of hydroquinone were added in 3 portions within 15 minutes. The mixture was stirred under reflux for 30 minutes. In the course of cooling to room temperature, a solid precipitated out and was filtered off with suction through a D3 suction filter. The filter residue was washed repeatedly with heptane. Subsequently, the residue was dried overnight in a vacuum drying cabinet at 50° C. and 100 mbar under a nitrogen atmosphere. 30 g of product were obtained in the form of a mixture of VIa+XVa. The filtrate was concentrated by evaporation at 140° C. and 5 mbar. 145 g of further product were obtained in the form of a mixture of VIa+XVa.

$^1$H NMR (400 MHz, 16 scans, CDCl$_3$):
VIa: δ=4.70 ppm, 2H, —CH$_2$—N(C$_{18}$H$_{37}$)—CH$_2$—O—
δ=3.73 ppm, 2H, —CH$_2$—N(C$_{18}$H$_{37}$)—CH$_2$—O—
XVa: δ=4.74 ppm, 2H, —CH$_2$—N(C$_{18}$H$_{37}$)—CH$_2$—O—
δ=3.86 ppm, 2H, —CH$_2$—N(C$_{18}$H$_{37}$)—CH$_2$—O—

The integrals of the spectra give rise to the following weight ratios:
VIa:XVa in the residue: 9:1
VIa:XVa in the filtrate: 1:1

Example 4

Tetrahydrobenzoxazine of the Formula IIIa

A 2000 ml four-neck flask was initially charged with 615 g of 2-methyl-4-polyisobutenylphenol (based on the commercially available high-reactivity polyisobutene Glissopal® 1000 with an Mn of 1000) at room temperature in 500 ml of toluene. 107 g of N,N-di(isobutoxymethyl)-N-methylamine from example 1 were added rapidly. The flask contents were stirred at 80° C. for 30 minutes. The solution was concentrated by evaporation at 120° C. and 5 mbar. 650 g of product were obtained in the form of an oil which can then be washed with methanol to remove small amounts of amine/aldehyde condensation products formed as a by-product.

$^1$H NMR (400 MHz, 16 scans, CDCl$_3$):
δ=4.73 ppm, 2H, —CH$_2$—N(CH$_3$)—CH$_2$—O—
δ=3.87 ppm, 2H, —CH$_2$—N(CH$_3$)—CH$_2$—O—

Example 5

Tetrahydrobenzoxazine of the Formula IIIe

A 1000 ml four-neck flask was initially charged with 206 g of 2,4-di-tert-butylphenol at room temperature in 400 ml of toluene. 203 g of N,N-di(isobutoxymethyl)-N-methylamine from example 1 were added rapidly. The flask contents were stirred at 80° C. for 60 minutes. The solution was concentrated by evaporation at 120° C. and 5 mbar. 260 g of product were obtained.

$^1$H NMR (400 MHz, 16 scans, CD$_2$Cl$_2$):
δ=4.73 ppm, 2H, —CH$_2$—N(CH$_3$)—CH$_2$—O—
δ=3.90 ppm, 2H, —CH$_2$—N(CH$_3$)—CH$_2$—O—

Example 6

Tetrahydrobenzoxazines of the Formulae VIII+XVII

A 2000 ml four-neck flask was initially charged with 24 g of paraformaldehyde at room temperature in 200 ml of isobutanol. 615 g of Kerocom® PIBA (commercially available 65% by weight solution of polyisobutenylamine based on high-reactivity polyisobutene, Mn=1000, in Mihagol, an n-alkane mixture) were added rapidly. The flask contents were heated to reflux and stirred under reflux for 30 minutes. 200 ml of toluene were then added and the water formed was entrained out. 22 g of hydroquinone were added dissolved in 200 ml of n-butanol within 15 minutes. Subsequently, the mixture was stirred under reflux for 60 minutes. The solution was concentrated by evaporation at 140° C. and 5 mbar. 440 g of product were obtained.

1H NMR (400 MHz, 16 scans, $CDCl_3$):
VIII: $\delta$=4.70 ppm, 2H, —$CH_2$—N(PIB)-$CH_2$—O—
  $\delta$=3.73 ppm, 2H, —$CH_2$—N(PIB)-$CH_2$—O—
XVII: $\delta$=4.75 ppm, 2H, —$CH_2$—N(PIB)-$CH_2$—O—
  $\delta$=3.87 ppm, 2H, —$CH_2$—N(PIB)-$CH_2$—O—

The integrals of the spectra give rise to the following weight ratios:
VIII:XVII=1:1.1.

Example 7

Tetrahydrobenzoxazine of the Formula IIIb

A 2000 ml four-neck flask was initially charged with 550 g of 4-polyisobutenylphenol (based on the commercially available high-reactivity polyisobutene Glissopal® 1000 with an Mn of 1000) at room temperature in 500 ml of toluene. 107 g of N,N-di-(isobutoxymethyl)-N-methylamine from example 1 were added rapidly. The flask contents were stirred at 80° C. for 60 minutes. The solution was washed with methanol and concentrated by evaporation at 120° C. and 5 mbar. 517 g of product were obtained.

$^1$H NMR (400 MHz, 16 scans, $CDCl_3$):
$\delta$=4.72 ppm, 2H, —$CH_2$—N($CH_3$)—$CH_2$—O—
$\delta$=3.90 ppm, 2H, —$CH_2$—N($CH_3$)—$CH_2$—O—

Example 8

Tetrahydrobenzoxazine of the Formula Vd

A 4000 ml four-neck flask was initially charged with 52.8 g of paraformaldehyde at room temperature in 400 ml of isopropanol. 1990 g of Kerocom® PIBA (commercially available 65% by weight solution of polyisobutenylamine based on high-reactivity polyisobutene, Mn=1000, in Mihagol, an n-alkane mixture) were added within 78 minutes. The flask contents were heated to reflux and stirred under reflux for 40 minutes. Thereafter, 138.1 g of trimethylhydroquinone were added in portions at from 60 to 80° C. Subsequently, 100 ml of toluene were added and the mixture was heated under reflux for 2 hours. Once the mixture had been cooled to room temperature and the isopropanol phase had then been removed and discarded, 1000 ml of heptane were added. The solution was washed with water and methanol and dried over sodium sulfate. The dry solution was concentrated by evaporation at 140° C. and 5 mbar. 1414 g of product were obtained.

$^1$H NMR (400 MHz, 16 scans, $CDCl_3$):
$\delta$=4.70 ppm, 2H, —$CH_2$—N(PIB)-$CH_2$—O—
$\delta$=3.81 ppm, 2H, —$CH_2$—N(PIB)-$CH_2$—O—
$\delta$=2.12, 2.07 and 2.00 ppm, each 3H, —$CH_3$ on the aromatic

Example 9

Tetrahydrobenzoxazine of the Formula XXIIIa

A 500 ml four-neck flask was initially charged with 110 g of α, ω-bis(4-hydroxyphenyl)-polyisobutene with a central p-phenylene structural unit (Mn=2000) which had been prepared according to document (7) at room temperature in 100 ml of toluene. 21.5 g of N,N-di(isobutoxymethyl)-N-methylamine from example 1 were added rapidly. The flask contents were stirred at 80° C. for 60 minutes. The solution was washed with methanol and concentrated by evaporation at 80° C. and 5 mbar. 104 g of product were obtained.

$^1$H NMR (400 MHz, 16 scans, $CDCl_3$):
$\delta$=4.71 ppm, 2H, —$CH_2$—N($CH_3$)—$CH_2$—O—
$\delta$=3.88 ppm, 2H, —$CH_2$—N($CH_3$)—$CH_2$—O—

Example 10

Tetrahydrobenzoxazine of the Formula IIIf

A 2000 ml four-neck flask was initially charged with 24 g of paraformaldehyde at room temperature in 150 ml of isopropanol. 800 g of Kerocom® PIBA (commercially available 65% by weight solution of polyisobutenylamine based on high-reactivity polyisobutene, Mn=1000, in Mihagol, an n-alkane mixture) were added within 20 minutes. The flask contents were heated to reflux and stirred under reflux for 30 minutes. Thereafter, 66 g of 2-tert-butyl-4-methylphenol dissolved in 150 ml of isopropanol were added dropwise. Subsequently, the mixture was heated under reflux for another 2 hours. Once the mixture had been cooled to room temperature and the isopropanol phase had then been removed and discarded, the solution was concentrated by evaporation at 140° C. and 5 mbar. 574 g of product were obtained.

$^1$H NMR (400 MHz, 16 scans, $CDCl_3$):
$\delta$=4.80 ppm, 2H, —$CH_2$—N(PIB)-$CH_2$—O—
$\delta$=3.90 ppm, 2H, —$CH_2$—N(PIB)-$CH_2$—O—
$\delta$=2.12 ppm, 3H, —$CH_3$ on the aromatic

USE EXAMPLES

Example 11

Testing of the Thermal Stability of Turbine Fuel (Jet Fuel)

A turbine fuel of the specification Jet A according to ASTM D 1655 was used. The additization was effected with 100 mg/l of the tetrahydrobenzoxazines or tetrahydrobenzoxazine mixtures from preparation examples 4 and 6 to 10.

In a three-neck flask which had been equipped with stirrer, reflux condenser and thermometer, 5 l of air were first passed at room temperature through 150 ml of the fuel to be examined within 1 h. Subsequently, the fuel was heated to 140° C. with an oil bath and stirred at this temperature for a further 5 h. After cooling to room temperature, the entire amount of fuel was filtered through a 0.45 μm membrane filter. Subsequently, the filter residue was determined gravimetrically after drying in a drying cabinet at 115° C. for 45 min and subsequently drying under reduced pressure in a desiccator for 2 hours:

Blank value (without additive): 12.0 mg additized in accordance with the invention with 100 mg/l in each case of the following compounds:
Compound of the formula IIIa (preparation example 4): 4.6 mg
Compounds of the formulae VIII=XVII (preparation example 6): 2.1 mg
Compound of the formula IIIb (preparation example 7): 2.4 mg
Compound of the formula Vd (preparation example 8): 2.2 mg Compound of the formula XXIIIa (preparation example 9): 1.5 mg
Compound of the formula IIIf (preparation example 10): 1.0 mg The use of the inventive additive distinctly reduced the amount of particles formed by thermal stress on the turbine fuel.

Example 12

Improvement in the Thermal Stability of Turbine Fuel (Jet Fuel)

A turbine fuel based on the specification Jet A according to ASTM D 1655 was used. The thermal stability was tested according to the JFPOT breakpoint method according to ASTM D 3241. For the unadditized turbine fuel, a value of 240° C. was determined. With fuels which had each been additized with 100 mg/l in each case of an additive used in accordance with the invention and listed below, the following values were measured:
Compound of the formula IIIa (preparation example 4): 280° C.
Compound of the formula IIIb (preparation example 7): 270° C.
Compound of the formula Vd (preparation example 8): 270° C.
Compound of the formula XXIIIa (preparation example 9): 270° C.

Example 13

Testing of the Water Compatibility of Turbine Fuel

A turbine fuel of the specification Jet A-1 according to DEF STAN 91-91 was used.

According to DIN 51415 and ASTM D 1094, the water compatibility of the turbine fuel and hence the undesired tendency to form emulsions were determined after addition of 100 mg/l of the product from preparation example 6. To this end, 80 ml of the additized turbine fuel and 20 ml of water were agitated intensively in a defined manner.

Thereafter, the phase separation layers were assessed visually after each of 1, 5, 30 and 60 minutes. As early as 5 minutes after addition of water, full separation of fuel and water was obtained; no emulsion fractions remained.

A repetition with 100 mg/l of the product from preparation example 7 led to the same result.

Example 14

Testing of the Water Separation Properties of Turbine Fuel

A turbine fuel of the specification Jet A-1 according to DEF STAN 91-91 was used. The tendency of turbine fuels with regard to their water separation properties was tested according to ASTM D 3948 ("MSEP" test). A characteristic feature of these measurements is the use of a standard coalescence filter with final opacity measurement of the fuel phase. In the measurement, the additives used in accordance with the invention were tested in combination with the antioxidant 2,6-di-tert-butyl-4-methylphenol ("BHT") and the metal deactivator N,N'-disalicylidene-1,2-diaminopropane in a solvent customary for this purpose. The dosage of the additives used in accordance with the invention was in each case 215 mg/l (based on their 100% active substance content). The following ratings for the opacity behavior were determined [relative rating scale from 0 (worst mark) to 100 (best mark)]:
Blank value (without additive): 99
Compound of the formula IIIa (preparation example 4): 95
Compound of the formula IIIb (preparation example 7): 99
Compound of the formula Vd (preparation example 8): 94

No deteriorations in comparison with unadditized turbine fuel occurred.

What is claimed is:

1. An antioxidant for stabilizing mineral oil products and fuels against the action of light, oxygen and heat, comprising: a tetrahydrobenzoxazine of formula I

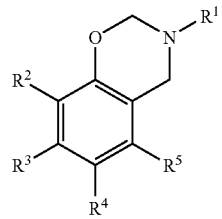

wherein
$R^1$ is a polyisobutene having a $M_n$ of from 200 to 40,000,
$R^2$, $R^3$, $R^4$ and $R^5$ are each independently hydrogen atoms, hydroxyl groups or hydrocarbyl radicals which have in each case from 1 to 3000 carbon atoms optionally having one or more heteroatoms from the group of O and S and/or one or more $NR^6$ moieties,
wherein the substituent $R^4$ may also be a radical of the formula Y

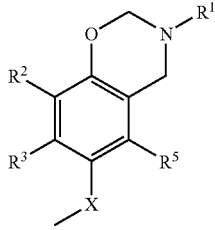

wherein $R^2$, $R^3$ and $R^5$ are each as defined above and X is a hydrocarbon bridging element which consists of one or more isobutene units or comprises one or more isobutene units, or
wherein the substituent $R^4$ may also be a radical of the formula Z or Z'
(Z)

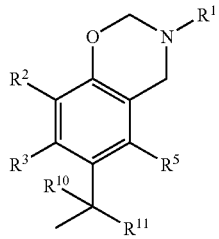

-continued

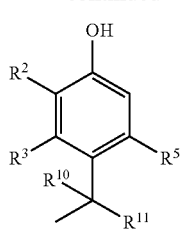

(Z')

wherein $R^2$, $R^3$ and $R^5$ are each as defined above and $R^{10}$, $R^{11}$ and $R^{12}$ are independently hydrogen or a $C_1$- to $C_{10}$-alkyl radical,
and wherein $R^2$ and $R^3$ or $R^3$ and $R^4$ or $R^4$ and $R^5$, together with the part-structure —O—CH$_2$—NR$^7$—CH$_2$— attached to the benzene ring, may also form a second tetrahydrooxazine ring, or the substituents $R^2$ and $R^3$ and $R^4$ and $R^5$, together with the part-structures —O—CH$_2$—NR$^7$—CH$_2$— and —O—CH$_2$—NR$^8$—CH$_2$— attached to the benzene ring, may also form a second and a third tetrahydrooxazine ring,
wherein $R^7$ and $R^8$ are each independently hydrocarbyl radicals which have in each case from 1 to 3000 carbon atoms and optionally have one or more heteroatoms from the group of O and S and/or one or more NR$^6$ moieties.

2. The antioxidant according to claim 1, wherein at least one further substituent selected from the group consisting of $R^2$, $R^3$, $R^4$, and $R^5$ is a polyisobutenyl radical having a number-average molecular weight $M_n$ of from 200 to 40 000.

3. The antioxidant according to claim 2, wherein two polyisobutenyl radicals having a number-average molecular weight $M_n$ of from 200 to 40 000 occur in the molecule as substituent $R^1$ and one selected from $R^2$ and $R^4$.

4. The antioxidant according to claim 1, wherein the remaining substituents from the group of $R^2$, $R^3$, $R^4$, $R^5$, $R^7$ and $R^8$ which are not substituents having polyisobutenyl radicals having a number-average molecular weight $M_n$ of from 200 to 40 000, each independently represent hydrogen atoms, hydroxyl groups or, when they are hydrocarbyl radicals, linear or branched $C_1$- to $C_4$-alkyl radicals.

5. The antioxidant according to claim 1, wherein the substituents $R^3$ and $R^4$ or $R^4$ and $R^5$, together with a part-structure —O—CH$_2$—NR$^7$—CH$_2$— form a second tetrahydrooxazine ring, wherein the —O of the part structure is positioned as $R^4$.

6. A turbine fuel or jet fuel, comprising: the antioxidant according to claim 1.

7. A method to improve the thermal stability of a turbine fuel or jet fuel, comprising: combining the antioxidant according to claim 1 with the turbine fuel or jet fuel.

8. A turbine fuel composition comprising a turbine fuel or jet fuel and at least one tetrahydrobenzoxazine of formula I as defined in claim 1.

9. An additive concentrate for turbine fuels or jet fuels, comprising:
    at least one tetrahydrobenzoxazine of formula I as defined in claim 1;
    optionally, at least one diluent; and
    optionally, at least one additive.

10. The antioxidant according to claim 1, wherein $R^1$ is a polyisobutene having a $M_n$, of from 500 to 40,000.

* * * * *

UNITED STATES PATENT AND TRADEMARK OFFICE
CERTIFICATE OF CORRECTION

PATENT NO. : 9,217,115 B2  Page 1 of 1
APPLICATION NO. : 11/996078
DATED : December 22, 2015
INVENTOR(S) : Arno Lange et al.

It is certified that error appears in the above-identified patent and that said Letters Patent is hereby corrected as shown below:

On the title page, Item (54) and Column 1, the Title is incorrect. Item (54) and Column 1 should read:

-- USE OF TETRAHYDROBENZOXAZINES AS STABILISERS --

Signed and Sealed this
Fifth Day of April, 2016

Michelle K. Lee
*Director of the United States Patent and Trademark Office*